United States Patent [19]

Lee et al.

[11] Patent Number: 5,543,019

[45] Date of Patent: Aug. 6, 1996

[54] METHOD OF COATING MEDICAL DEVICES AND DEVICE COATED THEREBY

[75] Inventors: Dosuk D. Lee, Brookline; William T. Conner, Somerville, both of Mass.

[73] Assignee: Etex Corporation, Cambridge, Mass.

[21] Appl. No.: 384,621

[22] Filed: Feb. 6, 1995

Related U.S. Application Data

[63] Continuation of Ser. No. 52,150, Apr. 23, 1993, abandoned.

[51] Int. Cl.$^6$ .................................................. C23C 14/46
[52] U.S. Cl. .............................. 204/192.15; 204/192.11; 204/192.14; 623/16
[58] Field of Search .......................... 204/190.11, 192.15, 204/192.14, 192.11; 623/16

[56] References Cited

U.S. PATENT DOCUMENTS

| | | | |
|---|---|---|---|
| 3,903,891 | 9/1975 | Brayshaw | 128/303.3 |
| 4,145,764 | 3/1979 | Suzuki et al. | 3/1.9 |
| 4,223,412 | 9/1980 | Aoyagi et al. | 3/1.9 |
| 4,778,721 | 10/1988 | Sliemers et al. | 428/336 |
| 4,908,030 | 3/1990 | Linkow et al. | 204/192.11 |
| 4,911,953 | 3/1990 | Hosonuma et al. | 427/377 |
| 4,944,754 | 7/1990 | Linkow et al. | 204/192.11 |
| 5,133,845 | 7/1992 | Vallana | 204/192.11 |
| 5,326,584 | 7/1994 | Kamel et al. | 427/491 |

OTHER PUBLICATIONS

David R. Cooley et al.,—The Journal of Prosthetic Dentistry—"The advantages of coated titanium implants prepared by radiofrequency sputtering from hydroxyapatite", Jan. 1992, vol. 67, No. 1, pp. 93–100.

L. Torrisi and G. Foti—Appl. Phys. Lett.—"keV ion sputtering of hydrozyapatite", 62(3), 18 Jan. 1993, pp. 237–239.

J.L. Ong et al.,—Biomaterials—"Structure, solubility and bond strength of thin calcium phosphate coatings produced by ion beam sputter deposition", 1992, vol. 13, No. 4, pp. 249–255.

W.R. Lacefield—Ann. N.Y. Acad. of Sciences—"Hydroxyapatite Coatings", 1988, pp. 72–81.

J.L. Ong et al.—The 17th Annual Meeting of the Society for Biomaterials—"Properties of calcium–phosphate coatings produced by ion–beam sputter deposition", May 1–5, 1991, p. 4.

E.D. Rigney—the 15th Annual Meeting of the Society for Biomaterials—"Characterization of a thin film sputter–deposited from a hydroxylapatite target", Apr. 28–May 2, 1989, p. 159.

*Primary Examiner*—Anthony McFarland
*Attorney, Agent, or Firm*—Fish & Richardson P.C.

[57] ABSTRACT

The invention features a method of depositing a coating on a medical device. The method includes: a) placing the medical device in an evacuated chamber, b) introducing a noble gas into the chamber, c) providing at least one target in the chamber, spaced from the device, and d) sputter depositing a coating onto the device by applying power to the target so that the noble gas forms a plasma in the vicinity of the target and material is sputtered from the target by ion bombardment and deposited on the device.

In another aspect, the invention features a medical device having a coating deposited by a plasma sputtering process. Preferably, the coating is a calcium containing compound.

33 Claims, 1 Drawing Sheet

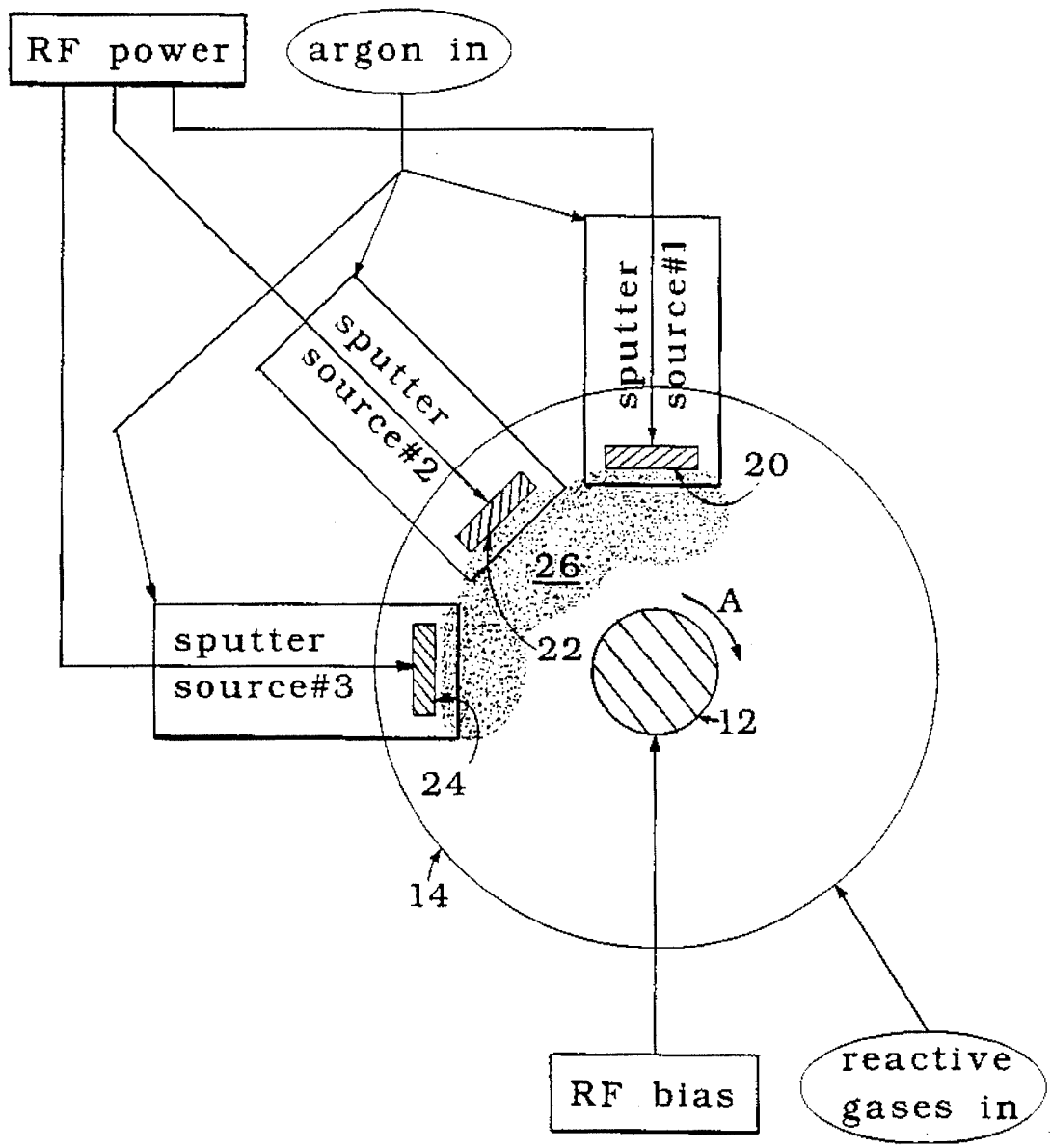

5,543,019

METHOD OF COATING MEDICAL DEVICES AND DEVICE COATED THEREBY

This is a continuation of application Ser. No. 08/052,150, filed on Apr. 23, 1993, now abandoned.

BACKGROUND OF THE INVENTION

The present invention relates to medical devices, in particular bone and dental implants.

Medical devices which are implanted in a patient's body, e.g., orthopedic and dental implants, are typically coated to improve their biocompatibility and to promote fixation of the implant to the bone. In recent years, such devices have been commercially coated with hydroxyapatite. These coatings provide a surface suitable for the ingrowth of bone tissue, resulting in more secure fixation of the implant to the existing bone.

Hydroxyapatite coatings are commercially applied by thermal plasma spraying. Plasma sprayed coatings are generally thick, e.g., about 50 to 70 microns, porous, and only moderately well adhered to the implant. These coatings tend to enhance the quality of the bone-implant interface. However, the sprayed coatings may lack mechanical strength, resistance to dissolution, and may be difficult to apply to irregular surfaces, as spraying is generally a line-of-sight process.

Ion beam sputtering has been proposed as a method of coating medical implants with hydroxyapatite, e.g., as described in U.S. Pat. Nos. 4,944,754 and 4,908,754. However, ion beam sputtering does not allow the chemical composition and physical properties of the coating to be readily controlled.

SUMMARY OF THE INVENTION

The inventor has found that the properties of biocompatible coatings on medical implants can be improved by depositing the coatings using a plasma sputtering process.

Advantageously, the chemical composition of the coating can be varied by the introduction of reactive gases during the sputtering process, allowing the solubility of the coating in body fluids, as well as other properties, to be widely varied. The ability to carefully control the solubility of the coating allows implants to be customized for different applications. For example, in some applications high solubility is desired, e.g., to allow the coating to dissolve away as bone grows around the implant, providing direct bone to implant contact, or for drug delivery, whereas in other applications it is critical that the coating not dissolve over extended use.

Further, the crystallinity and porosity of the coating can be readily varied, to suit a given application, by altering the parameters of the sputtering process. Plasma sputtering also allows deposition of a very thin, uniform coating, typically on the order of 1 micron, having excellent adhesion to the implant. These coatings also provide significantly better coverage of irregular surfaces than thermal plasma sprayed coatings.

Accordingly, in one aspect the invention features a method of depositing a coating on a medical device. The method includes: a) placing the medical device in an evacuated chamber, b) introducing a noble gas into the chamber, c) providing at least one target in the chamber, spaced from the device, and d) sputter depositing a coating onto the device by applying power to the target so that the noble gas forms a plasma in the vicinity of the target, causing ions from the plasma to bombard the target and sputter material from the target, a portion of which material is deposited onto the device.

In preferred embodiments, more than one target is provided. Preferably, the targets include compounds which contain at least one element selected from the group consisting of calcium, phosphorus, oxygen, hydrogen, fluorine, and titanium. More preferably, the compounds include calcium, phosphorus, oxygen, and either hydrogen or fluorine. It is further preferred that one or more reactive gases be introduced during sputtering. These gases, or the atoms comprising them, will be incorporated, with the sputtered material from the targets, into the film deposited on the implant. Thus, the introduction of reactive gases during sputtering can be used to control the stoichiometry of the deposited coating. Preferred reactive gases include hydrogen, oxygen, water vapor and phosphine.

Preferably, the coating deposited by the process of the invention is a calcium containing compound. More preferably, the chemical composition of the coating is in the calcium-phosphorus-oxygen-(hydrogen or fluorine) system, i.e., the composition preferably contains each of these elements. Preferred coatings in this system include hydroxyapatite $[Ca_{10}(PO_4)_6(OH)_2]$, amorphous calcium phosphate, tricalcium phosphate, fluorapatite, chloroapatite and carbonated apatites. Other preferred calcium containing compounds include calcium oxide and calcium titanate. The coating preferably is thin, more preferably from 0.1 to 3 microns, and has a low porosity.

In further preferred embodiments, the device is rotated during sputtering to insure uniform deposition over the surface of the device, the device is heated during sputtering, and the power applied to the targets is radio frequency (RF) power.

In other preferred embodiments, an RF bias is applied to the device, i.e., RF power is applied between the walls of the chamber and the device to produce a plasma near the device. The RF bias may be applied prior to sputtering, to clean the device and thereby improve adhesion of the coating. Alternatively or in addition, the RF bias may be applied during sputtering, to ion bombard the coating as it is being formed, making it denser and less porous. It is further preferred that the sputtering process be "magnetron sputtering", i.e., that a magnetic field be created at the surface of each target to confine the plasma to a smaller region near the target. This tends to increase the sputtering rate, and thus the deposition rate, and reduce heating of the device by the plasma, which may be undesirable in some applications.

In another preferred embodiment, the method further includes the step of, after sputtering, heat treating the coated device. The device may be heated under vacuum or a reducing atmosphere, or treated hydrothermally, i.e., sealed in a high pressure, high temperature vessel partially filled with water and heated.

In another aspect, the invention features a medical device having a coating deposited by a plasma sputtering process. Preferably, the coating is a calcium containing compound. More preferably, the chemical composition of the coating is in the calcium-phosphorus-oxygen-(hydrogen or fluorine) system, i.e., the composition preferably contains each of these elements. Preferred coatings in this system include hydroxyapatite $[Ca_{10}(PO_4)_6(OH)_2]$, amorphous calcium phosphate, tricalcium phosphate, fluorapatite, chloroapatite and carbonated apatites. Other preferred calcium containing compounds include calcium oxide and calcium titanate. The coating preferably is thin, more preferably from 0.1 to 3 microns, and has a low porosity.

Other features and advantages of the invention will be apparent to those skilled in the art from the following detailed description and from the claims.

DESCRIPTION OF THE PREFERRED EMBODIMENTS

DRAWING

The drawing is first briefly described.

The FIGURE is a schematic top view of a plasma sputtering system according to one embodiment of the invention.

SPUTTERING APPARATUS

A preferred apparatus for plasma sputtering a coating onto a medical device, e.g., a medical implant, is shown schematically in the FIGURE. A medical implant 12 is placed inside a chamber 14. The implant may be a metal, e.g., formed of titanium alloy or chrome cobalt, a ceramic, e.g., sintered or unsintered hydroxyapatite or other calcium phosphates, or it may be a composite material.

The chamber contains one or more sputtering sources (three are shown), which are preferably magnetron sputtering sources. Suitable magnetron sputtering sources are commercially available from AJA International, North Scituate, Mass. Each sputtering source includes a target (targets 20, 22, 24 in the FIGURE). Implant 12 is preferably mounted about 5 to 15 cm from the targets.

SPUTTERING PROCESS

Targets are selected to provide the elements which are desired in the coating composition. Preferably, at least one of the targets comprises a calcium containing compound, as calcium is believed to promote fixation of the implant to the surrounding bone. Preferred coatings are calcium phosphates, and thus it is preferred that the targets be selected to provide a calcium phosphate coating. When several sputtering sources are used, as shown, targets of different compositions can be used to provide a coating which contains elements from each of the target compositions. Alternatively, multiple targets having the same composition can be used to increase the deposition rate. It is simplest, but not necessarily most effective, to use a target with the same stoichiometry as that desired in the coating. For example, an hydroxyapatite target may be used to deposit an hydroxyapatite coating. However, the deposited coating typically contains excess calcium, relative to the hydroxyapatite target.

To adjust the stoichiometry of the coating deposited from the targets, reactive gases may be introduced into the chamber during sputtering, as shown. In the case of hydroxyapatite, a combination of hydrogen, oxygen and phosphine gases would preferably be introduced to balance the excess calcium in the coating with hydrogen, oxygen and phosphorus. Alternatively, extra phosphorus can be added by using a second target which is phosphorus rich, relative to hydroxyapatite, e.g., calcium pyrophosphate ($Ca_2P_2O_7$). A wide variety of combinations of targets and reactive gases can be used to obtain desired coating compositions.

Preferably, before the implant is mounted in the chamber the surface of the implant is thoroughly cleaned. Any conventional high vacuum compatible cleaning method may be used. For example, the implant may be etched in a solution of 20% nitric acid and 2% hydrofluoric acid, rinsed in distilled water, ultrasonically cleaned in trichloroethane, and rinsed with a succession of toluene, acetone and ethanol.

Referring again to the FIGURE, the cleaned implant 12 is mounted inside chamber 14 on a motor driven rotary feedthrough, which rotates the device (arrow A) to assist in the production of a uniform coating. The chamber is then evacuated, preferably to a pressure of less than $10^{-6}$ torr. If desired, the implant is then cleaned at the molecular level by applying an RF bias to the implant in an argon or argon/oxygen atmosphere at a pressure of 5 to 500 millitorr, typically approximately 10 millitorr.

Next, a noble gas is introduced to the chamber, preferably at a flow rate of from 10 to 100 sccm (standard $cm^3$/min). Argon is typically the chosen noble gas, as it is inexpensive and readily available relative to other noble gases, and is heavy enough to provide adequate sputtering rates for most applications. However, if higher sputtering rates are required, these can be provided by using a heavier noble gas, e.g., xenon. If desired, reactive gases are added at this point. The operating pressure of the system, after all gases are introduced, is preferably from about 1 to 500 millitorr, typically about 10 millitorr.

RF power is then applied to each of the sputtering sources. Preferably from 2 to 500 W is delivered to each sputtering source.

Application of power to the targets causes a plasma 26 to be formed in front of each target, resulting in ion bombardment and sputtering of material (mostly in atomic form, with some molecular component) from each target. The material is sputtered into the chamber, and some of it is deposited, along with some fraction of the reactive gases (if any are present), on the implant. The magnetic field created by permanent magnets located within the magnetron sputtering source localizes the plasma close to each target.

After a coating of a desired thickness is deposited on the implant, power delivery to the targets is discontinued, and the implant may be removed from the chamber, subjected to any desired post-treatment, and used.

In addition to deposition time, the thickness of the coating will depend upon a number of other factors, including the gas pressure and composition, target material, target to substrate distance and RF power applied to the sputter sources. A desired thickness can be readily obtained by varying these factors, as is well known in the sputtering art. Preferred thickness are from about 0.1 to 3 microns.

The composition of an obtained coating can be determined, if desired, by infrared spectroscopy and electron microscopy. Film crystallinity can be determined using X-ray diffraction. The adherence of the coating to the implant may be tested using a lap shear test, e.g., ASTM 1104-87. Preferred coatings have lap shear strengths of from about 4500 to 4900 PSI.

Preferred coatings have low porosity. Porosity may be reduced by applying an RF bias to the implant during sputtering, as shown in the FIGURE. This results in ion bombardment of the coating, which sputters away some of the film as it is being deposited, decreasing the deposition rate, but which also increases the density and decreases the porosity of the coating.

The implant may be heated during sputtering. This tends to increase the crystallinity of the deposited coating, by increasing the diffusion rate of atoms on the coating surface. The implant temperature may be increased by a few hundred degrees centigrade, often enough to improve crystallinity, by applying an RF bias to the implant. Higher temperatures, e.g., up to 1000° C., may be achieved by other methods, including mounting the substrate on a heated surface, using heating lamps or an infrared laser, or heating by RF induction.

The crystallinity of the coating may also be increased by post-deposition heat treatment. The implant may be heated to between 500° and 950° C. under vacuum, preferably at a pressure below $10^{-6}$ torr, or in an inert or reducing atmosphere. Alternatively, the implant may be hydrothermally treated, i.e., sealed in a high pressure, high temperature vessel partially filled with water and heated. Preferably, the vessel is heated to 100° to 250° C. To ensure that none of the coating is removed during hydrothermal treatment, it is preferred that a powder having a stoichiometry similar to that of the coating is added to the water before the vessel is sealed. For example, if the coating is hydroxyapatite, hydroxyapatite powder, or tricalcium phosphate powder (which converts to hydroxyapatite under hydrothermal conditions) could be used.

Other embodiments are within the claims. For example, the implant may be cooled during sputtering, e.g., by water cooling, for applications in which it is desirable to maintain the implant at a low temperature.

We claim:

1. A plasma sputtering method of depositing a coating on a medical device comprising the steps of:
   a) placing the medical device in a chamber;
   b) introducing a noble gas into the chamber;
   c) providing a target comprising calcium and phosphorous in the chamber, spaced from the device;
   d) introducing a reactive gas into the chamber; and
   e) applying power to the target so that the noble gas forms a plasma in the vicinity of the target, causing ions in the plasma to eject material from the target, a portion of which material is deposited onto the device to create a coating comprising hydroxyapatite.

2. The method of claim 1 wherein a plurality of targets are provided.

3. The method of claim 2 wherein said targets do not have the same chemical composition.

4. The method of claim 1 wherein said reactive gas is selected from the group consisting of oxygen, hydrogen water vapor and phosphine.

5. The method of claim 1 wherein said target further comprises a compound which contains at least one element selected from the group consisting of oxygen, hydrogen, fluorine, and titanium.

6. The method of claim 1 wherein the device is rotated during sputtering.

7. The method of claim 1 further comprising the step of heating the device during sputtering.

8. The method of claim 1 further comprising the step of cooling the device during sputtering.

9. The method of claim 1 wherein the power applied to the target is RF power.

10. The method of claim 1 wherein an RF bias is applied to the device prior to or during sputtering.

11. The method of claim 1 wherein a magnetic field is created at the surface of each target.

12. The method of claim 1 further comprising the step of, after sputtering, heat treating the device to increase the crystallinity of the deposited coating.

13. The method of claim 12 wherein the device is heated under vacuum or in a reducing atmosphere.

14. The method of claim 12 wherein the device is treated hydrothermally, using a mixture of water and a calcium containing powder.

15. The method of claim 1 wherein the coating comprises calcium, phosphorus, oxygen, and hydrogen atoms.

16. The method of claim 1 wherein the coating comprises calcium, phosphorus, oxygen and fluorine atoms.

17. The method of claim 1 wherein the coating further comprises a compound selected from the group consisting of amorphous calcium phosphate, tricalcium phosphate, fluorapatite, chloroapatite, carbonated apatites, calcium oxide, and calcium titanate.

18. The method of claim 1 wherein the device is formed of a metal.

19. The method of claim 18 wherein the metal is selected from the group consisting of titanium alloys, chrome cobalt alloys and stainless steel.

20. The method of claim 1 wherein the device is formed of a ceramic.

21. The method of claim 20 wherein the ceramic is a calcium phosphate compound.

22. The method of claim 21 wherein the ceramic is hydroxyapatite.

23. A medical device having a coating deposited by the process of claim 1.

24. The device of claim 23 wherein the coating comprises calcium, phosphorus, oxygen, and hydrogen atoms.

25. The device of claim 23 wherein the coating comprises calcium, phosphorus, oxygen and fluorine atoms.

26. The device of claim 23 wherein the coating comprises a compound selected from the group consisting of hydroxyapatite, amorphous calcium phosphate, tricalcium phosphate, fluorapatite, chloroapatite, carbonated apatites, calcium oxide, and calcium titanate.

27. The device of claim 23 wherein the device is formed of a metal.

28. The device of claim 27 wherein the metal is selected from the group consisting of titanium alloys, chrome cobalt alloys and stainless steel.

29. The device of claim 23 wherein the device is formed of a ceramic.

30. The device of claim 29 wherein the ceramic is a calcium phosphate compound.

31. The device of claim 30 wherein the ceramic is hydroxyapatite.

32. The method of claim 1 wherein said device comprises glass.

33. The device of claim 23 wherein said device comprises glass.

* * * * *

UNITED STATES PATENT AND TRADEMARK OFFICE
CERTIFICATE OF CORRECTION

PATENT NO.   : 5,543,019

DATED        : August 6, 1996

INVENTOR(S)  : DoSuk D. Lee and William T. Conner

It is certified that error appears in the above-identified patent and that said Letters Patent is hereby corrected as shown below:

Col. 4, line 51, replace "1104-87" with --1044-87--;

Col. 5, claim 3, lines 40-41, delete "do not have the same chemical composition" and add --have different chemical compositions relative to each other--.

Signed and Sealed this

Third Day of December, 1996

Attest:

BRUCE LEHMAN

*Attesting Officer*   Commissioner of Patents and Trademarks